United States Patent [19]

Miller et al.

[11] Patent Number: 4,567,312
[45] Date of Patent: Jan. 28, 1986

[54] PROCESS FOR PRODUCING ALKYLBENZENES

[75] Inventors: Stephen J. Miller, San Francisco; Sue D. Pandey, Berkeley, both of Calif.

[73] Assignee: Chevron Research Company, San Francisco, Calif.

[21] Appl. No.: 573,741

[22] Filed: Jan. 25, 1984

Related U.S. Application Data

[63] Continuation-in-part of Ser. No. 470,425, Feb. 28, 1983, abandoned.

[51] Int. Cl.$^4$ ................................................ C07C 2/52
[52] U.S. Cl. ..................................... 585/419; 208/138; 585/455
[58] Field of Search ................. 585/419, 455; 208/138

[56] References Cited

U.S. PATENT DOCUMENTS 3,397,137  8/1968  Pickert et al. .................. 208/138
3,783,123  1/1974  Young .......................... 208/254 H
4,325,808  4/1982  Kim et al. ....................... 208/65

FOREIGN PATENT DOCUMENTS 895280  3/1972  Canada .

Primary Examiner—Curtis R. Davis
Attorney, Agent, or Firm—D. A. Newell; S. R. La Paglia; E. A. Schaal

[57] ABSTRACT

Paraffins having a carbon number in excess of 10 are converted to aromatics, such as n-alkylbenzenes, over a dehydrocyclization catalyst comprising a large-pore zeolite containing at least one Group VIII metal. This process is carried out at a pressure of less than 100 psig. The dehydrocyclization catalyst can contain an alkaline earth metal selected from the group consisting of barium, strontium, and calcium. Preferably, the dehydrocyclization catalyst has from 8 to 10 percent by weight barium and from 0.2 to 1.0 percent by weight platinum, and the large-pore zeolite is a type L zeolite.

11 Claims, No Drawings

PROCESS FOR PRODUCING ALKYLBENZENES

This application is a continuation-in-part of U.S. application Ser. No. 470,425 filed Feb. 28, 1983, now abandoned.

BACKGROUND OF THE INVENTION

The invention relates to a new process for the production of alkylbenzenes.

Processes for producing biodegradable detergents are important because non-biodegradable detergents remain undissolved in sewage. When non-biodegradable detergents are aerated, large quantities of foam result. The diluted detergents solution often enter subsurface waters, which ultimately feed into the underground water strata, which serve many cities as a source of water supply. Occasionally, these detergents turn up in tap water in sufficient quantities to cause the water to foam at the tap.

To meet the public's demand for pure water, the petrochemical industry has attempted to develop biodegradable detergents. Alkylaryl-based detergents are more readily degradable by sewage bacteria if the alkyl substituent on the phenyl nucleus is of a simple, straight chain configuration than if it is of a more complex, branched chain structure. For example, detergent compounds with an alkyl side chain, such as:

are more likely to be bacterially digested than detergents of the same chemical composition but in which the isomeric alkyl radical is a more highly branched chain, such as:

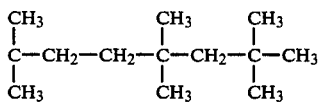

These biodegradable detergents are generally manufactured either: (1) by using molecular sieves or urea adduction to isolate $C_9$ to $C_{18}$ n-paraffins from mixtures containing the paraffins and converting the n-paraffins to an olefin-acting compound, such as a monohalogenated paraffin or a mono-olefin; or (2) by cracking of saturated paraffin waxes to produce a linear olefin. These olefin-acting compounds are then used to alkylate a mono-cyclic aromatic, such as benzene, and the resultant alkylaromatic is sulfonated and neutralized to form the desired detergent.

Catalytic reforming is a well known process that involves raising the octane rating of a naphtha. The reactions that occur during reforming include: dehydrogenation of cyclohexanes, dehydroisomerization of alkylcyclopentanes, dehydrocyclization of acyclic hydrocarbons, dealkylation of alkylbenzenes, isomerization of paraffins, and hydrocracking of paraffins. While most reforming catalysts contain platinum on an alumina support, some people have proposed using large-pore zeolites as a support. These large-pore zeolites have pores large enough for hydrocarbons in the gasoline boiling range to pass through. Catalysts based on these zeolitic supports have been commercially unsuccessful.

It would be advantageous if longer hydrocarbons could be subjected to dehydrocyclization to form alkylbenzenes for use in detergents, enhanced oil recovery surfactants, and lube oil additives. The end use would determine the preferred feed. For instance, hydrocarbons containing 16 to 22 carbon atoms per molecule would be useful feeds for a process making detergent-type products, while hydrocarbons containing from 25 to 40 carbon atoms per molecule would be ideal feeds for a process making lube oil additives.

SUMMARY OF THE INVENTION

The present invention is based on the discovery that n-alkylbenzenes can be formed by contacting n-paraffins having a carbon number in excess of 10 with a dehydrocyclization catalyst, comprising a large-pore zeolite containing at least one Group VIII metal, under conditions which favor dehydrocyclization. The dehydrocyclization catalyst gives superior selectivity for converting the long chained paraffins to alkylbenzenes than shown in prior art processes. The dehydrocyclization catalyst also gives commercially viable run length.

Preferably, the dehydrocyclization catalyst contains an alkaline earth metal selected from the group consisting of barium, strontium, and calcium (more preferably, barium). More preferably, the dehydrocyclization catalyst contains: (a) a type L zeolite containing from 0.1 to 5.0 percent by weight platinum (preferably from 0.2 to 1.0 percent by weight platinum) and from 0.1 to 40.0 percent by weight barium (preferably from 8 to 10 percent by weight barium); and (b) a nonacidic inorganic binder.

In one preferred embodiment, n-paraffins having a carbon number in excess of 10 contacted at a pressure of less than 100 psig with a dehydrocyclization catalyst under conditions which favor dehydrocyclization to produce n-alkylbenzenes. The dehydrocyclization catalyst comprises: (1) a type L zeolite containing from 8 to 10 percent by weight barium and from 0.2 to 1.0 percent by weight platinum; and (2) a nonacidic inorganic binder selected from the group consisting of silica, alumina, and aluminosilicates.

DESCRIPTION OF THE PREFERRED EMBODIMENTS

In its broader aspect, the present invention involves the dehydrocyclization of paraffins having a carbon number in excess of 10 to form alkylbenzenes. The dehydrocyclization is carried out using a dehydrocyclization catalyst comprising a large-pore zeolite and a Group VIII metal.

Feedstock used in the present invention contains paraffins having a carbon number in excess of 10 (preferably about 16 to 22 for detergents or 25 to 40 for lube oil). Preferably, these paraffins are n-paraffins.

Preferably, the feedstock is substantially free of sulfur, nitrogen, metals, and other known poisons for reforming catalysts. This catalyst is especially sensitive to sulfur. The feedstock can be made substantially free of sulfur, nitrogen, metals, and other known poisons by conventional hydrofining techniques, plus sorbers that remove sulfur compounds.

The long paraffins can be contacted with the catalyst in either a fixed bed system, a moving bed system, a fluidized system, or a batch system. Either a fixed bed system or a moving bed system is preferred. In a fixed bed system, the preheated paraffins are passed into at least one reactor that contains a fixed bed of the catalyst. The flow of the paraffins can be either upward, downward, or radial. The pressure is below about 400 psig, with the preferred pressure being below about 100 psig. The preferred temperature is from about 370° C. to about 540° C. The liquid hourly space velocity (LHSV) is from about 0.1 hr$^{-1}$ to about 10 hr$^{-1}$, with a preferred LHSV of from about 0.3 hr$^{-1}$ to about 3 hr$^{-1}$. Enough hydrogen is used to insure an H$_2$/HC ratio of up to about 20:1. The preferred H$_2$/HC ratio is from about 2:1 to about 6:1. Dehydrocyclization produces hydrogen. Thus, additional hydrogen is not needed except when the catalyst is pre-reduced and when the paraffins are first introduced. Once dehydrocyclization is underway, part of the hydrogen that is produced is recycled over the catalyst.

The catalyst is a large-pore zeolite charged with at least one Group VIII metal. The preferred Group VIII metal is platinum, which is more selective for dehydrocyclization and which is more stable under reforming reaction conditions than other Group VIII metals. The catalyst should contain between 0.1% and 5% platinum of the weight of the catalyst, preferably from 0.2% to 1.0%.

The term "large-pore zeolite" is defined as a zeolite having an effective pore diameter of from 6 to 15 Angstroms. The preferred pore diameter is from 7 to 9 Angstroms. Type L zeolite, zeolite X, and zeolite Y are thought to be the best large-pore zeolites for this operation. Type L zeolite is described in U.S. Pat. No. 3,216,789. Zeolite X is described in U.S. Pat. No. 2,882,244. Zeolite Y is described in U.S. Pat. No. 3,130,007. U.S. Pat. No. 3,216,789; 2,882,244; and 3,130,007 are hereby incorporated by reference to show zeolites useful in the present invention. The preferred zeolite is type L zeolite.

Type L zeolites are synthesized largely in the potassium form. These potassium cations are exchangeable, so that other type L zeolite can be obtained by ion exchanging the type L zeolite in appropriate solutions. It is difficult to exchange all of the original cations, since some of these cations are in sites which are difficult to reach. Preferably, the potassium is ion exchanged with an alkaline earth metal, which can be either barium, strontium, or calcium. Barium is preferred because the resulting catalyst has a high activity, a high selectivity for dehydrocyclization, and a high stability. Preferably, the barium should constitute from 0.1% to 35% of the weight of the zeolite, more preferably from 1% to 20%.

An inorganic oxide can be used as a carrier to bind the large-pore zeolite. This carrier can be natural, synthetically produced, or a combination of the two. Preferred loadings of inorganic oxide are from 5% to 50% of the weight of the catalyst. Useful carriers include silica, alumina, and aluminosilicates.

After the desired Group VIII metal or metals have been introduced, the catalyst is treated in air at about 260° C. and then reduced in hydrogen at temperatures of from 200° C. to 700° C., preferably 300° C. to 620° C. At this stage the dehydrocyclization catalyst is ready for use in the dehydrocyclization process.

EXAMPLES

The invention will be further illustrated by the following examples which set forth a particularly advantageous method and composition embodiments. While the examples are provided to illustrate the present invention, they are not intended to limit it.

EXAMPLE I

An n-C$_{16}$ paraffin was contacted with a dehydrocyclization catalyst at 900° F., 2 LHSV, 1 atmosphere pressure, and 6 H$_2$/HC, with a conversion of 9 percent. The product composition is shown in Table I. Gas chromatography-mass spectrometry analysis showed about 30% selectivity to n-decylbenzene.

The dehydrocyclization catalyst was formed by putting a type L zeolite of crystallite size greater than 1000 Angstroms as determined by X-ray diffraction into a ten-times excess of a solution of 0.3 molar Ba(NO$_3$)$_2$ in H$_2$O. This solution was placed in a closed container in an oven for three hours at 80° C., then the solids were filtered and washed with a ten-times excess of water. The solids were then dried overnight at 250° F. in air, calcined at 1100° F. for 16 hours in air, and screened to 24/80 mesh, and then a solution of Pt(NH$_3$)$_4$(NO$_3$)$_2$ in water was added to 0.8 percent Pt by weight of zeolite. The resulting catalyst was dried overnight at 250° F. in air, and calcined for two hours at 500° F. in air. The catalyst was prereduced before the hydrocarbon feed was introduced.

TABLE 1

| Product, % of Converted n-C$_{16}$ | |
|---|---|
| C$_4$- | 18 |
| Paraffins | |
| C$_5$-C$_{13}$ | 10 |
| C$_{14}$-C$_{15}$ | 5 |
| Olefins | |
| C$_{16}$ | 22 |
| Aromatics | |
| C$_6$-C$_{12}$ | 6 |
| C$_9$-C$_{10}$ (Olefinic) | 8 |
| Naphthalene | 1 |
| C$_{16}$ n-decylbenzene | 30 |

EXAMPLE II

A hexadecane feed was contacted with the dehydrocyclization catalyst of Example I at 900° F., 4 LHSV, 100 psig, and 6 H$_2$/HC, with a conversion in the range of 44 to 51 percent. The product composition is shown in Table II.

TABLE II

| Products % of Converted n-C$_{16}$ | Wt Percent |
|---|---|
| Decylbenzene | 3 |
| 1-methyl nonylbenzene (branched sidechain) | 2 |
| Undecylcyclopentane (C$_{16}$ naphthene) | 4 |
| Branched, saturated hexadecanes | 20 |
| Biphenyl | 8 |
| Naphthalene | 5 |
| C$_6$-C$_9$ aromatics (subst. benzenes) | 23 |
| C$_1$-C$_5$ | 12 |
| Unidentified | 23 |

EXAMPLE III

A hexadecane feed was contacted with the dehydrocyclization catalyst of Example I at atmospheric pressure and 6H$_2$/HC, at various temperatures and space velocities. The results are shown in Table III.

TABLE III

| | | | |
|---|---|---|---|
| Temperature, °F. | 900 | 900 | 800 |
| LHSV | 0.33 | 1.0 | 0.33 |
| Conversion, % | 86 | 43 | 52 |
| C$_7$+, Wt % | 73 | 90 | 86 |
| Selectivities, Wt % | | | |

TABLE III-continued

| | | | | |
|---|---|---|---|---|
| Monosubstituted Alkylbenzenes | | | | |
| n = 1 | 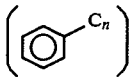 | 1.8 | 0.5 | 0.7 |
| 2 | | 1.4 | 0.4 | 0.8 |
| 3 | | 0.5 | 0.4 | 0.5 |
| 4 | | 0.3 | 0.8 | 0.7 |
| 5 | | 0.2 | 0.4 | 0.4 |
| 6 | | 0.3 | 0.5 | 0.3 |
| 7 | | 0.4 | 0.4 | 0.5 |
| 8 | | 0.4 | 0.3 | 0.4 |
| 9 | | 0.6 | 0.5 | 0.4 |
| 10 | | 2.5 | 7.2 | 2.9 |
| Total | | 8.4 | 11.4 | 7.6 |
| Disubstituted Alkylbenzenes | | | | |
| n = 1 | 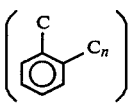 | 1.7 | 0.8 | 0.7 |
| 2 | | 2.1 | 1.8 | 1.7 |
| 3 | | 1.2* | 0.9 | 1.3 |
| 4 | | 0.3 | 0.2 | 0.3 |
| 5 | | 0 | 0.3 | 0.5 |
| 6 | | 0.2 | 0.4 | 0.3 |
| 7 | | 0.8 | 0.3 | 0.3 |
| 8 | | 0 | 0.3 | 0 |
| 9 | | 2.5 | 3.6 | 2.8 |
| Total | | 8.8 | 8.6 | 7.9 |
| Unidentified Alkylbenzene | | 0.4 | 1.9 | 0.1 |
| Total Alkylbenzenes | | 17.6 | 21.9 | 15.6 |
| $C_6^-$ | | 31 | 23 | 27 |
| $C_7^+$ Aromatics | | | | |
| 1-2 Ring | | 36 | 44 | 25 |
| 3 + Rings | | 19 | 16 | 7 |
| $C_7^+$ Paraffins | | | | |
| Normal | | 4 | 6 | 26 |
| Iso | | 0 | 0.1 | 4 |
| $C_7^+$ Olefins | | 1 | 1 | 2 |
| Unidentified | | 9 | 10 | 9 |

*Includes o-diethylbenzene.

While the present invention has been described with reference to specific embodiments, this application is intended to cover those various changes and substitutions which may be made by those skilled in the art without departing from the spirit and scope of the appended claims.

What is claimed is:

1. A process for producing n-alkylbenzenes comprising contacting n-paraffins having a carbon number in excess of 15, with a dehydrocyclization catalyst, comprising a large-pore zeolite containing at least one Group VIII metal, under conditions which favor dehydrocyclization to produce said n-alkylbenzenes.

2. A process according to claim 1 wherein said process is carried out at a pressure of less than 100 psig and a temperature of from about 370° C. to about 540° C.

3. A process according to claim 1 wherein said paraffins have from 16 to 22 carbon atoms per molecule.

4. A process according to claim 1 wherein said paraffins have from 25 to 40 carbon atoms per molecule.

5. A process according to claim 1 wherein said large-pore zeolite has an apparent pore size of from 7 to 9 Angstroms.

6. A process according to claim 5 wherein said large-pore zeolite is selected from the group consisting of zeolite X, zeolite Y and type L zeolite.

7. A process according to claim 6 wherein said large-pore zeolite is a type L zeolite.

8. A process according to claim 1 wherein said dehydrocyclization catalyst contains an alkaline earth metal selected from the group consisting of barium, strontium, and calcium.

9. A process according to claim 8 wherein said alkaline earth metal is barium and wherein said Group VIII metal is platinum.

10. A process according to claim 9 wherein said dehydrocyclization catalyst has from 8 to 10 percent by weight barium and from 0.2 to 1.0 percent by weight platinum.

11. A process for producing n-alkylbenzenes comprising: contacting n-paraffins, having a carbon number in excess of 15, at a pressure of less than 100 psig and a temperature of from about 370° C. to about 540° C. with a dehydrocyclization catalyst under conditions which favor dehydrocyclization to produce n-alkylbenzenes, wherein said dehydrocyclization catalyst comprises:
 (1) a type L zeolite containing from 8 to 10 percent by weight barium and from 0.2 to 1.0 percent by weight platinum; and
 (2) a nonacidic inorganic oxide binder selected from the group consisting of silica, alumina, and aluminosilicates.

* * * * *